(12) United States Patent
Louwagie et al.

(10) Patent No.: US 11,904,175 B2
(45) Date of Patent: Feb. 20, 2024

(54) FEEDTHROUGH INSULATOR CAP FOR MEDICAL DEVICE BATTERY

(71) Applicant: Medtronic, Inc., Minneapolis, MN (US)

(72) Inventors: Jeffrey J. Louwagie, Minnetonka, MN (US); Richard W. Swenson, Edina, MN (US); Joel Hoepner, Plymouth, MN (US); David J. DeSmet, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/173,448

(22) Filed: Feb. 23, 2023

(65) Prior Publication Data

US 2023/0191139 A1    Jun. 22, 2023

Related U.S. Application Data

(62) Division of application No. 16/809,030, filed on Mar. 4, 2020, now abandoned.

(Continued)

(51) Int. Cl.
*A61N 1/375* (2006.01)
*A61N 1/362* (2006.01)
(Continued)

(52) U.S. Cl.
CPC ........... *A61N 1/3754* (2013.01); *A61N 1/362* (2013.01); *H01M 10/052* (2013.01);
(Continued)

(58) Field of Classification Search
CPC . Y02E 60/10; H01M 50/543; H01M 10/0454; H01M 10/0413; H01M 10/0431;
(Continued)

(56) References Cited

U.S. PATENT DOCUMENTS 9,281,507 B2 * 3/2016 Bruch ................... H01M 50/24
10,727,454 B2 7/2020 Bruch et al.
(Continued)

OTHER PUBLICATIONS

International Search Report and Written Opinion of International Application No. PCT/US2020/02450, dated Jun. 30, 2020, 9 pp.
(Continued)

*Primary Examiner* — Thiem D Phan
(74) *Attorney, Agent, or Firm* — Shumaker & Sieffert, P.A.

(57) ABSTRACT

A battery configured to support a relatively high rate of energy discharge relative to its capacity for energy intensive therapy delivery. The battery includes a feedthrough insulator cap disposed within the interior of the battery on at least a portion of a ferrule, at least a portion of an insulator, and at least a portion of a pin, which define a feedthrough extending through an enclosure of the battery; a first electrode disposed within the enclosure and electrically coupled to the pin; a second electrode disposed within the enclosure and separated a distance from the first electrode; and an electrolyte disposed between the first electrode and the second electrode. During operation of the battery, the feedthrough insulator cap reduces dendrite formation on at least a portion of the ferrule, the pin, or both.

6 Claims, 7 Drawing Sheets

Related U.S. Application Data

(60) Provisional application No. 62/846,833, filed on May 13, 2019.

(51) Int. Cl.
| | | |
|---|---|---|
| *H01R 13/59* | (2006.01) | |
| *H01M 10/052* | (2010.01) | |
| *H01M 50/172* | (2021.01) | |
| *H01M 50/552* | (2021.01) | |
| *H01M 50/186* | (2021.01) | |
| *H01M 50/191* | (2021.01) | |
| *H01M 50/184* | (2021.01) | |

(52) U.S. Cl.
CPC ....... *H01M 50/172* (2021.01); *H01M 50/186* (2021.01); *H01M 50/552* (2021.01); *H01R 13/59* (2013.01); *H01M 50/184* (2021.01); *H01M 50/191* (2021.01); *H01R 2201/12* (2013.01); *Y10T 29/49108* (2015.01)

(58) Field of Classification Search
CPC ............ H01M 10/287; Y10T 29/49108; Y10T 29/4911; Y10T 29/53135; A61N 1/3754
USPC ......... 29/623.1, 623.2, 623.5, 729, 730, 746
See application file for complete search history.

(56) References Cited

U.S. PATENT DOCUMENTS

| | | | |
|---|---|---|---|
| 2002/0150817 A1* | 10/2002 | Grubb | H01M 50/566 |
| | | | 429/94 |
| 2004/0191621 A1 | 9/2004 | Heller, Jr. | |
| 2018/0138463 A1 | 5/2018 | Bruch et al. | |
| 2020/0360702 A1 | 11/2020 | Louwagie et al. | |

OTHER PUBLICATIONS

Office Action from U.S. Appl. No. 16/809,030 dated Nov. 23, 2022, 6 pp.

* cited by examiner

FEEDTHROUGH INSULATOR CAP FOR MEDICAL DEVICE BATTERY

This application is a divisional of U.S. patent application Ser. No. 16/809,030, filed on Mar. 4, 2020, which claims the benefit of U.S. Provisional Application Ser. No. 62/846,833, filed on May 13, 2019, the entire content of each of which is incorporated herein by reference.

TECHNICAL FIELD

This disclosure relates to batteries, such as batteries used in medical devices.

BACKGROUND

Medical devices such as implantable medical devices (IMDs) include a variety of devices that deliver therapy (such as electrical stimulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or to power circuitry for monitoring a physiological parameter of a patient and controlling the functionality of the medical device.

SUMMARY

In general, the disclosure is directed to a battery for a medical device, such as an IMD, and techniques for manufacturing the battery. The battery may include a high-rate primary battery having a lithium metal anode and a feedthrough insulator cap reflowed onto a portion of a feedthrough ferrule of the battery (the "ferrule") and a portion of a unipolar electrical feedthrough pin of the battery (the "pin"). The shape of the feedthrough insulator cap prior to reflow provides coverage of the ferrule and pin to reduce occurrence of electrical shorting due to, for example, lithium ion dendrite growth. Thus, the feedthrough insulator cap may increase the useable life of the battery.

In some examples, a battery may include an enclosure defining an interior of the battery and a feedthrough aperture open to an exterior of the battery; a ferrule extending through the feedthrough aperture and coupled to the enclosure; an insulator extending through the ferrule to the exterior of the battery; a pin extending through the insulator from the interior of the battery to the exterior of the battery, the insulator electrically insulating the pin from the ferrule; a feedthrough insulator cap disposed within the interior of the battery on at least a portion of the ferrule, at least a portion of the insulator, and at least a portion of the pin; a first electrode disposed within the enclosure and electrically coupled to the pin; a second electrode disposed within the enclosure and separated a distance from the first electrode; and an electrolyte disposed between the first electrode and the second electrode.

In some examples, a medical device may include an outer housing and a high-rate primary battery within the outer housing. The high-rate primary battery may be configured to supply power to one or more electronic components of the medical device. The high-rate primary battery may include an enclosure defining an interior of the battery and a feedthrough aperture open to an exterior of the battery; a ferrule extending through the feedthrough aperture and coupled to the enclosure; an insulator extending through the ferrule to the exterior of the battery; a pin extending through the insulator from the interior of the battery to the exterior of the battery, the insulator electrically insulating the pin from the ferrule; a feedthrough insulator cap disposed within the interior of the battery on at least a portion of the ferrule, at least a portion of the insulator, and at least a portion of the interior segment of the pin; a first electrode disposed within the enclosure and electrically coupled to the pin; a second electrode disposed within the enclosure and separated a distance from the first electrode; and an electrolyte disposed between the first electrode and the second electrode.

In some examples, a method of assembling a battery includes positioning a feedthrough insulator cap on a feedthrough of the battery. The battery may include an enclosure, a first electrode, a second electrode, and an electrolyte. The enclosure may define the interior of the battery and a feedthrough aperture open to an exterior of the battery. The feedthrough includes a ferrule extending through the feedthrough aperture and coupled to the enclosure, an insulator extending through the ferrule to the exterior of the battery, and a pin extends through the insulator from the interior of the battery to the exterior of the battery, the insulator electrically insulating the pin from the ferrule. The first electrode may be disposed within the enclosure and electrically coupled to the pin. The second electrode may be disposed within the enclosure and separated a distance from the first electrode. The electrolyte may be disposed between the first electrode and the second electrode. The method also includes heating the feedthrough insulator cap to reflow the material of the feedthrough insulator cap onto at least a portion of a ferrule, at least a portion of an insulator, and at least a portion of an interior segment of a pin.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

In general, the disclosure is directed to battery for a medical device, such as an IMD. The battery may include a unipolar electrical feedthrough pin (the "pin") that protrudes through a feedthrough ferrule (the "ferrule"), for example, from an anode stack, through a cover of the battery, to an exterior of the cover. The battery includes a feedthrough insulator cap reflowed onto the ferrule and the pin (e.g., on the interior of the battery). As used herein, reflow or reflowing may include heating a polymeric material to at least a flowable state, such as a semi-solid or liquid state. In some examples, the battery is a primary battery not configured to be recharged. In some examples, the battery is configured to support a relatively high rate of energy discharge relative to its capacity to, for example, support energy intensive therapy delivery, such as high energy anti-tachyarrhythmia shocks, by the IMD. In some examples, the battery has a lithium chemistry.

The feedthrough insulator cap is configured to electrically insulate at least a portion of the ferrule from at least a portion of the pin (e.g., on the interior of the battery) to reduce or prevent dendrite formation during operation of the battery that may cause the battery to short circuit or otherwise fail. For example, in examples in which the battery includes a lithium chemistry, the potential difference at the pin and the ferrule may cause lithium ion plating at one of the pin and the ferrule. Lithium plating can result in the growth of lithium dendrites that can eventually produce a short circuit between the pin and the ferrule. The feedthrough insulator cap may at least increase the distance between exposed portions of the ferrule and exposed portion of the interior segment of the pin. The increased distance may reduce electrical shorting from dendrite formation during operation of the battery. In this way, the feedthrough insulator cap may increase the useable life of the battery.

Figure 1:
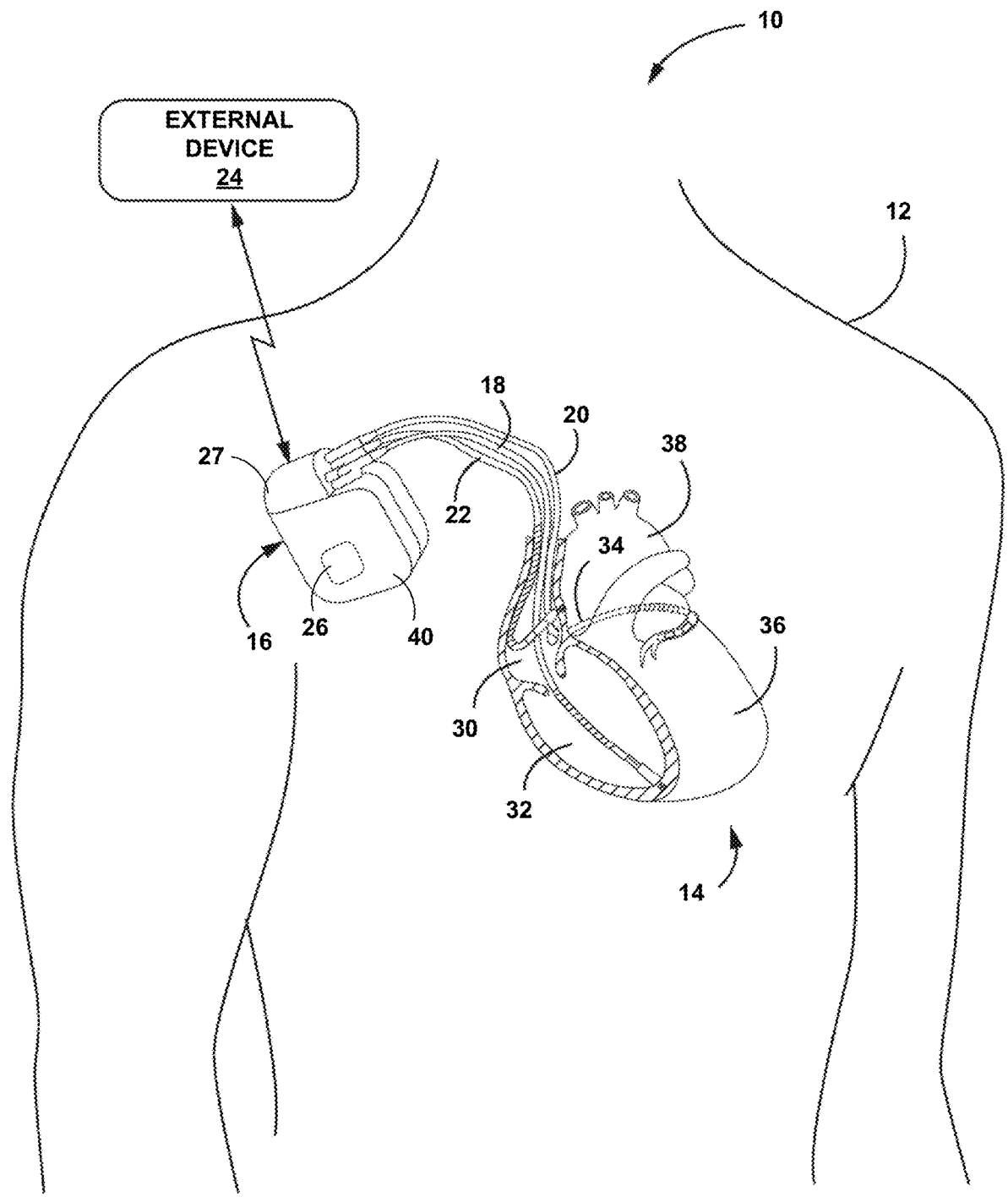
FIG. 1 is a conceptual diagram that illustrates an example medical device system that may be used to deliver therapy to a patient and/or sense one or more physiological parameters of a patient.
Figure 2:
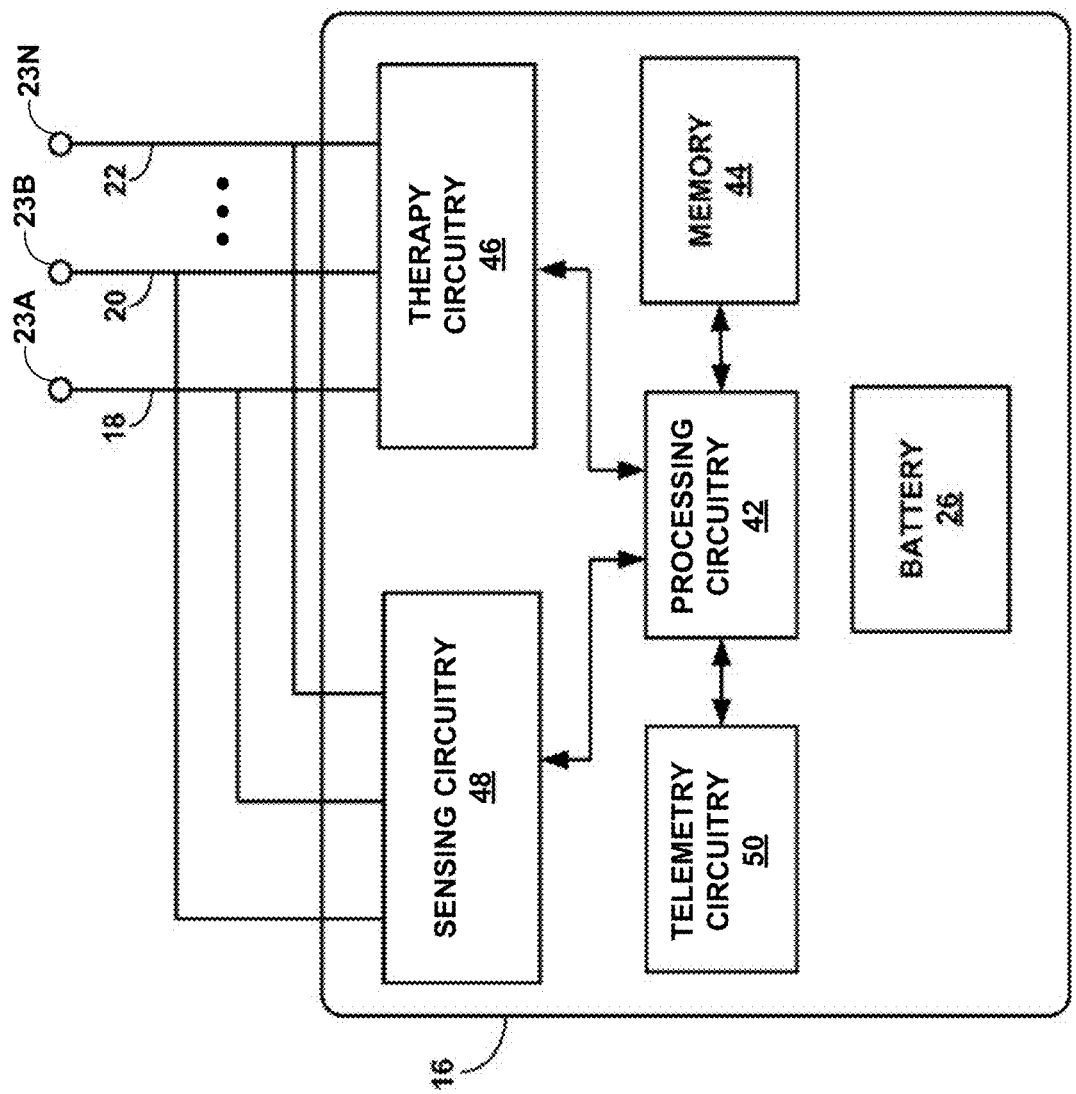
FIG. 2 is a schematic diagram illustrating components of one example IMD.

FIG. 1 is a conceptual diagram that illustrates an example medical device system 10 that may be used to provide therapy to patient 12 and/or sense physiological parameters of patient 12. Patient 12 ordinarily, but not necessarily, will be a human. Medical device system 10 may include implantable medical device (IMD) 16 and external device 24. In the example illustrated in FIG. 1, IMD 16 includes battery 26 positioned within housing 40 of IMD 16. FIG. 2 is a schematic diagram illustrating example components of IMD 16. As will be described below, battery 26 includes battery enclosure 58 (FIG. 3) in accordance with one or more examples of the disclosure.

While the examples in the disclosure are primarily directed to battery 26 employed in IMD 16, in other examples, battery 26 may be utilized with other IMDs. For example, battery 26 may be utilized with an implantable drug delivery device, an implantable monitoring device that monitors one or more physiological parameters of patient 12 without delivering therapy, or an implantable neurostimulator (e.g., a spinal cord stimulator, a deep brain stimulator, a pelvic floor stimulator, a peripheral nerve stimulator, or the like). In general, battery 26 may be attached to or implanted proximate to any medical device configured to be implanted in a body of a patient 12.

Moreover, while examples of the disclosure are primarily described with regard to IMDs, examples are not limited as such. Rather, examples of the batteries described herein may be employed in any electronic device, such as other implantable or non-implantable medical devices. For example, a battery according to some examples described herein may be employed to supply power to a medical device configured delivery therapy to a patent or sense physiological parameters of the patient externally or via a transcutaneously implanted lead or drug delivery catheter.

In the example depicted in FIG. 1, IMD 16 is electrically connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation pulses, while in other examples, IMD 16 may deliver cardioversion or defibrillation pulses, but not pacing pulses. In addition, in further examples, IMD 16 may deliver pacing pulses, cardioversion pulses, and defibrillation pulses.

IMD 16 may include electronics and other internal components necessary or desirable for executing the functions associated with IMD 16. For example, as shown in FIG. 2, in addition to battery 26, IMP 16 may include processing circuitry 42, memory 44, electrical therapy circuitry 46, sensing circuitry 48 and telemetry circuitry 50. Memory 44 of IMD 16 may include a non-transitory computer readable storage medium having instructions that, when executed by processing circuitry 42 of IMD 16, may cause it to perform various functions attributed to the device herein. For example, processing circuitry 42 of IMD 16 may control therapy circuitry 46 and sensing circuitry 48 according to instructions and/or data stored on memory to deliver therapy to patient 12 and perform other functions related to treating condition(s) of the patient with IMD 16.

Therapy circuitry 46 of IMD 16 may generate electrical signals that are delivered to patient 12 via one or more electrode(s) 23A, 23B, and 23N (collectively, "electrodes 23") on one or more of leads 18, 20, and 22, e.g., cardiac pacing signals, or cardioversion/defibrillation shocks. Sensing circuitry 48 of IMD 16 may monitor electrical signals from electrodes 23 on leads 18, 20, and 22 of IMD 16 in order to monitor electrical activity of heart 14. In one example, sensing circuitry 48 may include switching circuitry to select which of the available electrodes 23 on leads 18, 20, and 22 of IMD 16 are used to sense the heart activity. Additionally, sensing circuitry 48 of IMD 16 may include multiple detection channels, each of which may include an amplifier, as well as an analog-to-digital converter for digitizing the signal received from a sensing channel (e.g., electrogram signal processing by processing circuitry of the IMD).

Telemetry circuitry 50 of IMD 16 may include any suitable hardware, firmware, software or any combination thereof for communicating with another device, such as external device 24 (FIG. 1). Under the control of processing circuitry 42 of IMD 16, telemetry circuitry 50 may receive downlink telemetry from and send uplink telemetry to external device 24 with the aid of an antenna, which may be internal and/or external.

The various electrical components of IMD 16 may be coupled to battery 26, which may include a rechargeable or non-rechargeable (primary) battery. A non-rechargeable battery may be capable of holding a charge for several years, while a rechargeable battery may be inductively charged from an external device (e.g., on a daily or weekly basis). In general, battery 26 may supply power to one or more electrical components of IMD 16, such as, e.g., processing circuitry 42, telemetry circuitry 50, therapy circuitry 46 and/or sensing circuitry 48, to allow IMD 16 to deliver therapy to patient 12, e.g., in the form of monitoring one or more patient parameters and/or delivery of electrical stimulation. Battery 26 may include an enclosure (e.g., battery case) configured to physically separate the electrolyte and electrodes of battery 26 from other components within housing 40 of IMD 16.

In the example of FIG. 1, leads 18, 20, 22 that are coupled to IMD 16 may extend into heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and to a target region in right ventricle 32. Left ventricular (LV) coronary sinus lead 20 extends through one or more veins, the vena cava, right atrium 30, and into the coronary sinus 34 to a target region adjacent to the free wall of left ventricle 36 of heart 14. Right atrial (RA) lead 22 extends through one or more veins and the vena cava, and to a target region in right atrium 30 of heart 14. In some examples, IMD 16 may be a leadless device. For example, IMD 16 may be positioned within heart 14 at a target region. In some examples, IMD 16 may sense and deliver therapy to heart 14 from an extravascular location in addition to or instead of delivering stimulation via electrodes of intravascular leads 18, 20, 22, e.g., IMD 16 may be coupled to one or more leads that extend to substernal or other extravascular locations. In the illustrated example, there are no electrodes located in left atrium. However, other examples may include electrodes in left atrium.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical pulses. In some examples, IMD 16 may be programmed to deliver a progression of therapies (e.g., electrical pulses with increasing energy levels), until a fibrillation of heart 14 is stopped. IMD 16 may detect fibrillation by employing one or more fibrillation detection techniques known in the art. For example, IMD 16 may identify cardiac parameters of the cardiac signal (e.g., R-waves) and detect fibrillation based on the identified cardiac parameters).

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMP 16 via wireless communication using any techniques known in the art. Examples of communication techniques may include, for example, low frequency or radiofrequency (RF) telemetry, but other techniques are also contemplated. In some examples, external device 24 may include a programming head that may be placed proximate to the patient's body near the IMD 16 implant site in order to improve the quality or security of communication between IMD 16 and external device 24.

In the example depicted in FIG. 1, IMD 16 is electrically connected (or "coupled") to leads 18, 20, and 22. In the example, leads 18, 20, and 22 are connected to IMD 16 using the connector block 27. For example, leads 18, 20, and 22 are connected to IMD 16 using the lead connector ports in connector block 27. Once connected, leads 18, 20, and 22 are in electrical contact with the internal circuitry of IMD 16. Battery 26 may be positioned within the housing 40 of IMD 16. Housing 40 may be hermetically sealed and biologically inert. In some examples, housing 40 may be formed from a conductive material. For example, housing 40 may be formed from a material including, but not limited to, titanium, aluminum, stainless steel, among others.

Figure 3:
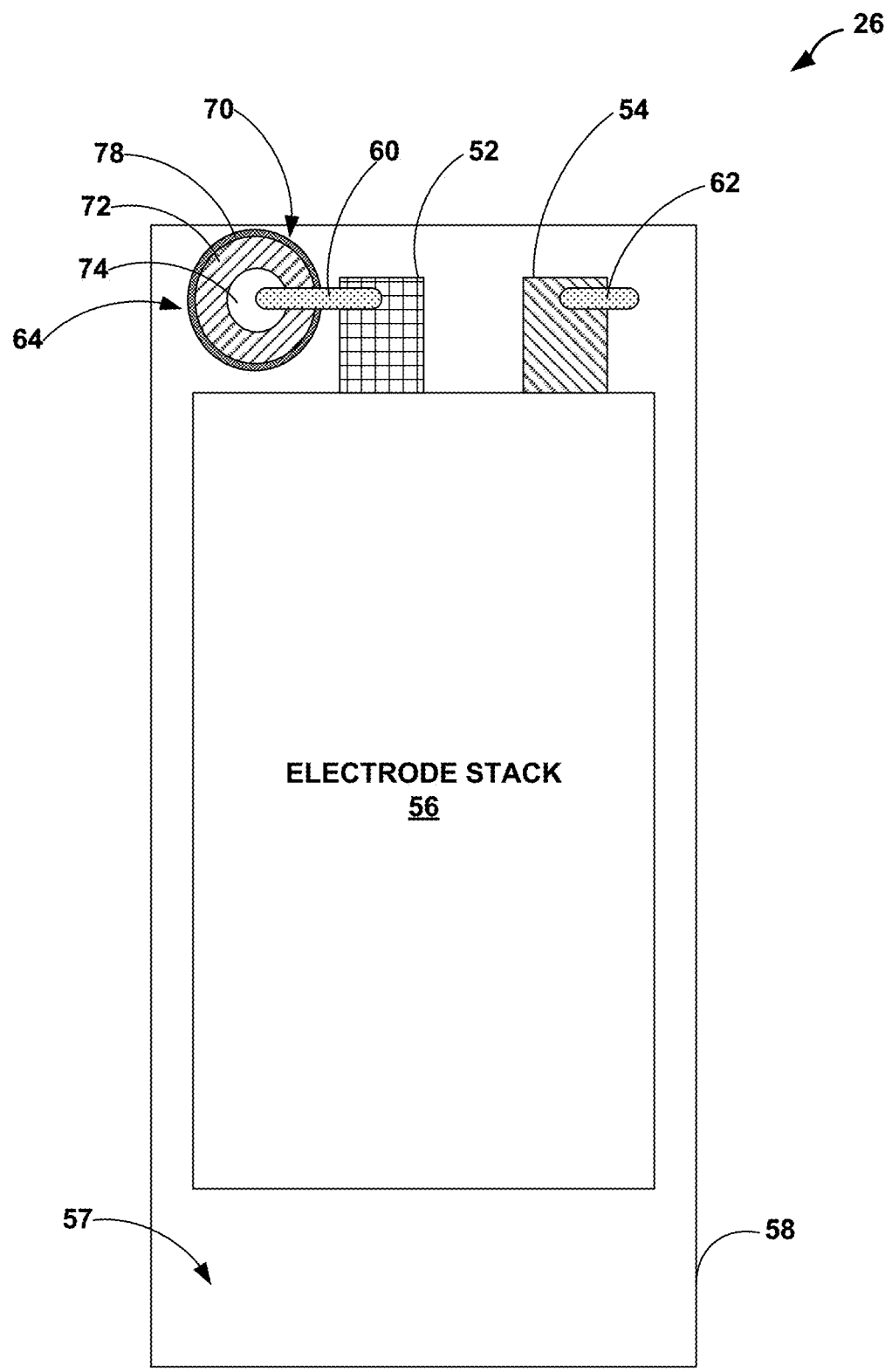
FIG. 3 is schematic diagram illustrating an example battery that may be used in a medical device.

FIG. 3 is a schematic diagram illustrating an example of battery 26 that may be used in IMD 16. As described above, battery 26 may be configured to supply power to one more electronic components of IMD 16. In some examples, battery 26 may be a lithium battery, such as a lithium metal battery or a lithium ion battery. In some examples, battery 26 may include a high rate primary lithium metal battery. In some examples, battery 26 may take the form of other types of batteries other than a lithium battery. Battery 26 includes anode stack 52, cathode stack 54, and electrodes (e.g., an electrode stack) 56. Enclosure 58 encloses these and other components of battery 26 to provide separation from the outside environment, e.g., the interior of housing 40 of IMD 16. In some examples, enclosure 58 may include a conductive metal or a multilayer enclosure including, for example, stainless steel, titanium, aluminum, or one or more corrosion resistant materials.

Electrodes 56 may include one or more first electrodes (e.g., anodes) and one or more second electrodes (e.g., cathodes). In some examples, electrodes 56 may include a plurality of anodes, each anode adjacent to one or more cathodes of a plurality of cathodes. The arrangement of anode stack 52, cathode stack 54, and electrodes 56 is for illustrative purposes. In some examples, anode stack 52, cathode stack 54, and electrodes 56 may be positioned within enclosure 58 in any suitable arrangement, such as a plurality of layers (of first and second electrodes), stacked, wound, folded, or combinations thereof. Electrodes 56 may include a metal substrate and any suitable electrode composition. For example, each anode of electrodes 56 may include a lithium metal anode, whereas each cathode of electrodes 56 may include manganese oxide or silver-vanadium oxide (SVO), or carbon monofluoride (CFx) or mixtures of CFx and SVO. The metal substrates of electrodes 56 may act as a current collectors and be a metal made from at least one of, but not limited to, aluminum, aluminum alloys, copper, copper alloys, titanium, titanium alloys, nickel, nickel alloys, and the like.

An electrolyte 57 may be disposed between the electrodes (e.g., between the first electrode(s) and the second electrode (s), between the plurality of anodes and the plurality of cathodes). Electrolyte 57 may be provided intermediate or between adjacent electrodes of electrodes 56. Electrolyte 57 may provide a medium through which ions (e.g., lithium ions) may travel. In one example, electrolyte 57 may be a liquid (e.g., a lithium salt dissolved in one or more non-aqueous solvents). In some examples, electrolyte 57 includes a mixture of dimethoxy-ethane and propylene carbonate in any suitable volume percent (vol %). In some examples, electrolyte 57 includes a lithium salt, such as $LiAsF_6$. Various other primary lithium battery electrolytes may be used according to other examples. For example, the lithium salt may be replaced with $LiPF_6$ or the solvent propylene carbonate may be replaced with ethylene carbonate.

In some examples, an electrode separator may be disposed between anodes and adjacent cathodes, such as, for example, a polypropylene/polyethylene or another polyolefin multilayer laminate that includes micropores formed therein to allow electrolyte and lithium ions to flow from one side of the separator to the other. In some examples, a solid electrolyte interface layer may be formed on the surface of either electrode adjacent to the separator. In some examples, the solid electrode interface layer may include an unsaturated cyclic carbonic acid ester, such as vinylene carbonate. Solid electrolyte interface layers may separate one or more electrodes of electrodes 56 from electrolyte 57, which may control the dissolution and plating or the uptake of lithium ions on the surfaces of the electrodes during charge/discharge cycles.

Each respective cathode of electrodes 56 is electrically coupled to cathode stack 54. In some examples, cathode stack 54 may be electrically coupled to a cathode pin 62. In some examples, cathode pin 62 may be electrically coupled to enclosure 58. Each respective anode of electrodes 56 is electrically coupled to anode stack 52. In some examples, anode stack 52 may be electrically coupled to feedthrough pin 60. Feedthrough pin 60 may extend from an interior segment of feedthrough pin 60, through a feedthrough member 64 extending through feedthrough aperture 70 ("aperture 70") defined by enclosure 58, to an exterior portion of feedthrough pin 60. In this way, enclosure 58 may define a first terminal of battery 26 and feedthrough pin 60 may define a second terminal of battery 26 to allow for electrical connection to components outside battery enclosure 58. Pins 60 and 62 may be wires or rods and may also include foil tabs, metalized polymer, or other suitable conductor such as a material including carbon or a conductive ceramic such as titanium nitride Feedthrough 64 may include an annular ferrule 72 ("ferrule 72") and an insulator 74. In some examples, ferrule 72 is coupled to aperture 70. For example, ferrule 72 may include a cylindrical annulus having a radially exterior surface, a radially interior surface, and an interior annular surface that is disposed within enclosure 58. The radially exterior surface of ferrule 72 may be coupled to aperture 70 by, for example, welding or an adhesive such as an epoxy. In some examples, ferrule 72 may include other geometries, such as rectilinear or irregular shapes. Ferrule 72 may include any suitable material configured to seal aperture 70. In some examples, ferrule 72 may include an electrically conductive metal, such as stainless steel, titanium, aluminum, or one or more corrosion resistant materials.

An insulator 74 may be coupled to the radially interior surface of ferrule 72. In some examples, insulator 74 may include a cylindrical annulus having a radially exterior surface, a radially interior surface, and an interior annular surface that is disposed within enclosure 58. The radially exterior surface of insulator 74 may be coupled to the radially interior surface of ferrule 72 by, for example, an adhesive, such as an epoxy, friction fit, or compression fit. The radially interior surface of insulator 74 may be coupled to feedthrough pin 60 by, for example, an adhesive, such as an epoxy, friction fit, or compression fit. In other words, feedthrough pin 60 may extend from an interior segment of feedthrough pin 60 (e.g., interior segment 86 in FIG. 4), through insulator 74, to an exterior portion of feedthrough pin 60 (e.g., exterior segment 87 in FIG. 4). In some examples, insulator 74 may include other geometries, such as rectilinear or irregular shapes. Insulator 74 may include any suitable non-electrically conductive material, such as, for example, glass, ruby, sapphire, or one or more materials that are electrically insulative and conducive to providing a hermetic seal. In this way, insulator 74 may electrically insulate feedthrough pin 60 from ferrule 72.

In some examples, a feedthrough overmold 78 may encase at least a portion of feedthrough 64, such as portions of ferrule 72 and insulator 74 exposed to the interior of enclosure 58, e.g., exposed to electrolyte 57. In some examples, feedthrough overmold 78 may encase at least a portion of feedthrough pin 60. Feedthrough overmold 78 may include any suitable material configured to reduce lithium dendrite formation on selected portions of ferrule 72, insulator 74, and/or feedthrough pin 60. During operation of battery 26, however, electrolyte 57 may penetrate beneath feedthrough overmold 78 and form lithium dendrites on the selected portions of ferrule 72, insulator 74, and/or feedthrough pin 60. To reduce dendrite formation underneath feedthrough overmold 78, battery 26 includes a feedthrough insulator cap 66.

Figure 4:
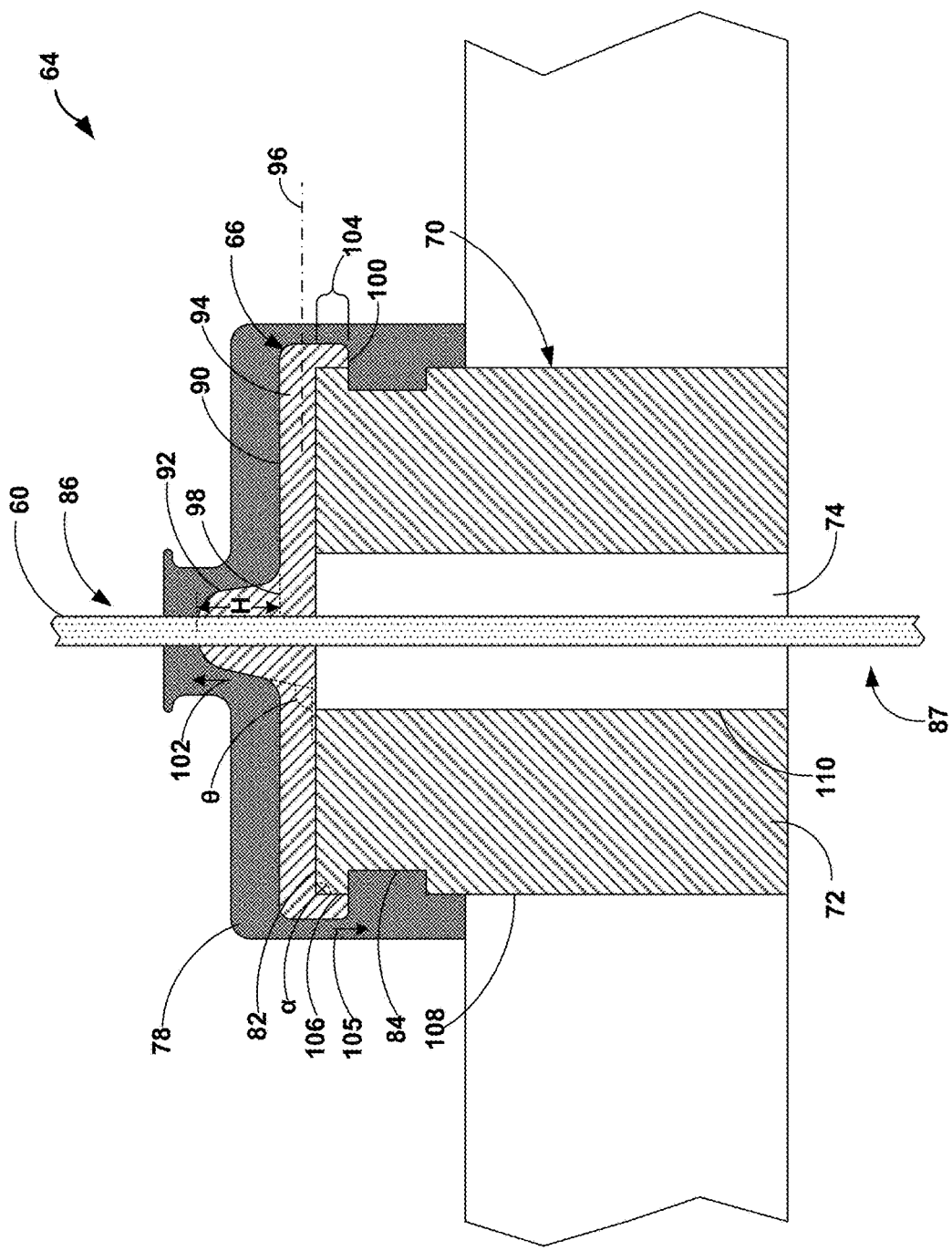
FIG. 4 is a conceptual diagram illustrating the feedthrough of the example battery illustrated in FIG. 3 after reflowing onto at least a portion of ferrule, at least a portion of insulator, and at least a portion of pin.

FIG. 4 is a conceptual diagram illustrating a cross-sectional view of feedthrough 64 that includes feedthrough insulator cap 66 after reflowing onto at least a portion of ferrule 72, at least a portion of insulator 74, and at least a portion of pin 60. Feedthrough insulator cap 66 may be disposed between feedthrough overmold 78 and at least a portion of ferrule 72, at least a portion of insulator 74, and at least a portion of pin 60. Feedthrough insulator cap 66 is configured to electrically insulate feedthrough 64 to at least increase the distance between exposed portions 84 of ferrule 72 and exposed portions of interior segment 86 of pin 60. Feedthrough insulator cap 66, during operation of battery 26, may reduce or prevent formation of dendrites on at least a portion of ferrule 72, pin 60, or both. In examples in which battery 26 includes a lithium chemistry, the dendrites may include lithium metal dendrites.

In some examples, feedthrough insulator cap 66 defines a brim region 90 and a crown region 92. Brim 90 may include an annular disk 94 extending substantially within a plane 96. Although disk 94 is illustrated as having an annular shape, disk 94 may include other geometries, such as rectilinear or irregular shapes. Additionally, or alternatively, although disk 94 is illustrated as substantially planar, in some example, disk 94 may include surface features, such as grooves or ridges, extending radially, circumferentially, or the like on one or more surfaces of disk 94. Brim 90 may define an interior edge 98 and an exterior edge 100. Crown 92 may be integrally formed with interior edge 98 of brim 90. In some examples, crown 92 may be separately formed from brim 90 and coupled to interior edge 98, for example, by adhesion, thermal welding, or sonic welding.

Crown 92 extends above plane 96 of disk 94 in a first direction 102. In some examples, crown 92 may extend above plane 96 at an angle θ within a range from about 90-degrees to about 135-degrees, such as about 100-degrees to about 120-degrees or about 102-degrees, relative to plane 96. The angle θ may be prior to or after reflowing (e.g., heating) feedthrough insulator cap 66. The angle θ may be selected to control reflow of crown 92, such as a capillary action which may cause at least a portion of crown 92 to travel in first direction 102 when heated to reflow. In some examples, a height H of crown 92 above plane of brim prior to or after reflowing is within a range between about 0.1 millimeters (mm) to about 5.0 mm, such as between about 0.3 mm to about 1.0 mm. The height H of crown 92 may be selected to control a path length between a portion of interior segment 86 of feedthrough pin 60 extending past crown 92 and portion 84 ferrule 72 extending below brim 90.

In some examples, brim 90 includes a deflection 104. Deflection 104 may extend below plane 96 of disk 94 in a second direction 105. Deflection 104 may include or define exterior edge 100 of brim 90. In some examples, prior to a reflow process, deflection 104 may extend below plane 96 of disk 94 at an angle α within a range from about 90-degrees to about 135-degrees relative to plane 96. By extending below plane 96, deflection 104 may overlap at least a portion of an exterior lip 106 of ferrule 72. In examples in which ferrule 72 includes a cylindrical annulus having a radially exterior surface 108, a radially interior surface 110, and an interior annulus 82 disposed within the enclosure of the battery, radially exterior surface 108 may be coupled to the feedthrough aperture 70 and feedthrough insulator cap 66 may be disposed over interior annulus 82 of the ferrule and at least a portion of radially exterior surface 108 (e.g., lip 106). Overlapping at least a portion of exterior lip 106 increases the path length from exposed portion 84 of ferrule 72 extending below feedthrough insulator cap 66 to interior segment 86 of pin 60 extending above insulator cap 66. Increasing the path length may reduce or prevent electrical shorting via dendrite formation from exposed portion 84 of ferrule 72 to interior segment 86 of pin 60, which may result in a short between ferrule 72 and pin 60.

Figure 5A:
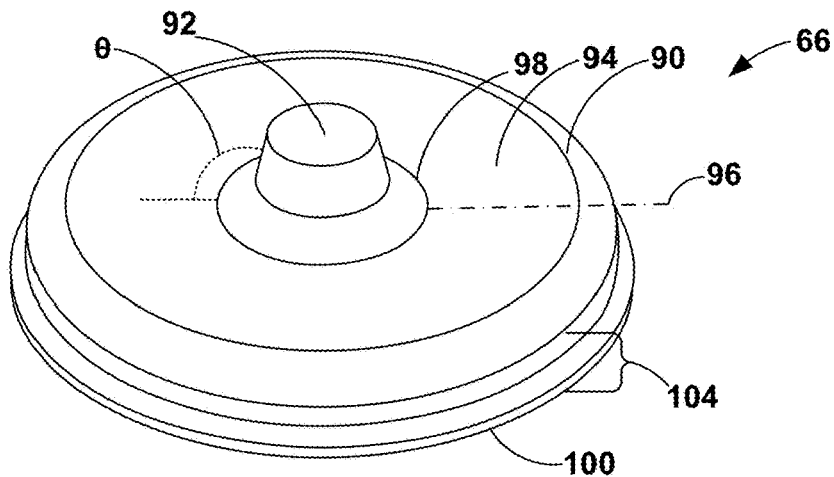
FIGS. 5A-5C are conceptual diagrams illustrating an example feedthrough insulator cap prior to reflowing.
Figure 5B:
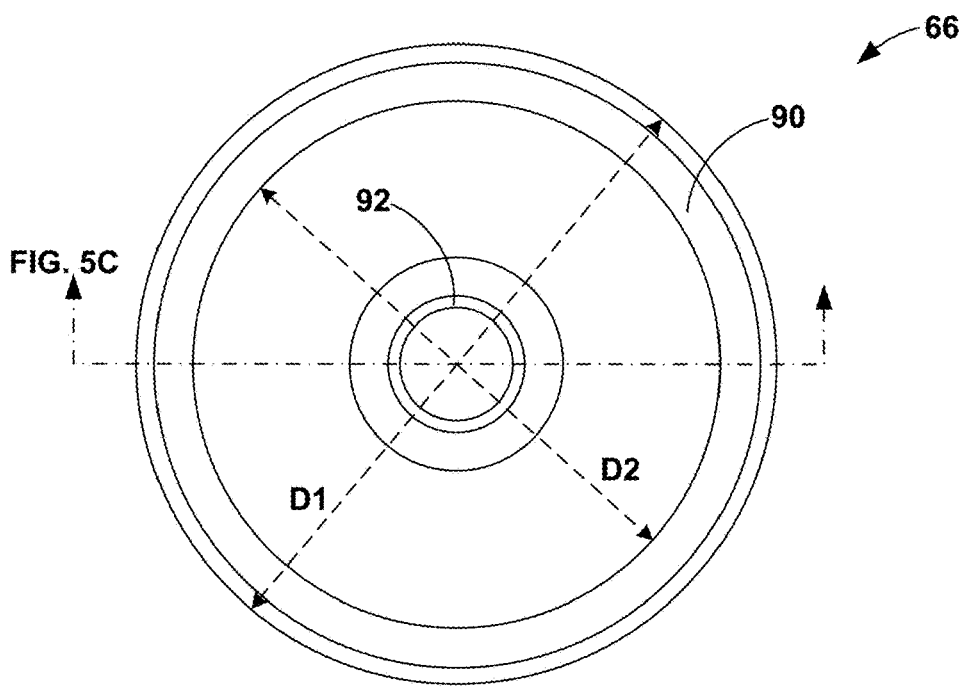
Figure 5C:
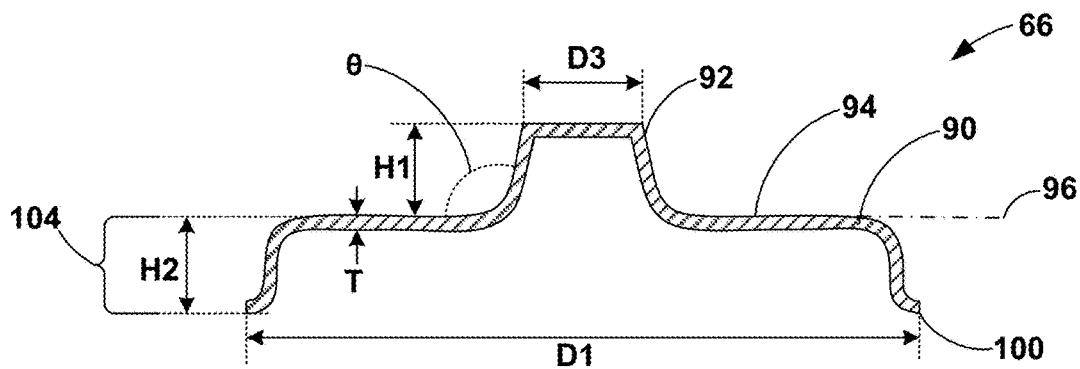

FIGS. 5A-5C are conceptual diagrams illustrating an example feedthrough insulator cap 66 prior to reflowing. As discussed above in reference to FIG. 4, feedthrough insulator cap 66 includes brim 90 and crown 92. Brim 90 includes disk 94 extending in plane 96. Brim 90 also defines interior edge 98 and exterior edge 100, and may include a deflection 104 extending below plane 96. Crown 92 extends above plane 96 at angle θ. In some examples, crown 92 may include an aperture through which a pin, e.g., pin 60, may extend.

As illustrated in FIG. 5B, brim 90 may define an outer diameter D1. In some examples, diameter D1 may be greater than an outer diameter of a ferrule, e.g., ferrule 72. In this way, feedthrough insulator cap 66 may be fitted over ferrule 72 prior to reflowing. In some examples, reflowing feedthrough insulator cap 66 may cause diameter D1 to shrink. For example, during reflowing, diameter D1 of feedthrough insulator cap 66 may shrink between about 1% to about 25%. In some examples, disk 94 of brim 90 may define a diameter D2. In some examples, diameter D2 may be substantially equal (e.g., equal or nearly equal) to an outer diameter of ferrule 72. In examples in which diameter D2 is substantially equal to an outer diameter of ferrule 72, planar disk 94 may lay substantially flat (e.g., flat or nearly flat) on an interior annulus (e.g., interior annulus 82) of ferrule 72 prior to and/or during reflowing. By laying substantially flat on interior annulus 82, feedthrough insulator cap 66 may contact an entire area defined by interior annulus 82 after reflowing.

As illustrated in FIG. 5C, crown 92 may have a diameter D3 and height H1. In examples in which crown 92 extends above plane 96 at an angle θ of 90-degrees, crown 92 may have a substantially constant diameter. In other examples, crown 92 may include a tip diameter at the tip of crown 92 and a different base diameter at the base of crown 92, e.g., where crown 92 meets disk 94. Height H1 of crown 92 may include any suitable height as described above in reference to FIG. 4. Deflection 104 may have a height H2. In some examples, height H2 of deflection 104 below plane 96 of brim 90 prior to reflowing may be within a range between about 0.1 millimeters (mm) to about 3.0 mm, such as between about 0.3 mm to about 1.0 mm. The height H2 of deflection 104 may be selected to control a path length between a portion of interior segment 86 of feedthrough pin 60 extending past crown 92 and portion 84 ferrule 72 extending below brim 90.

Figure 6C:
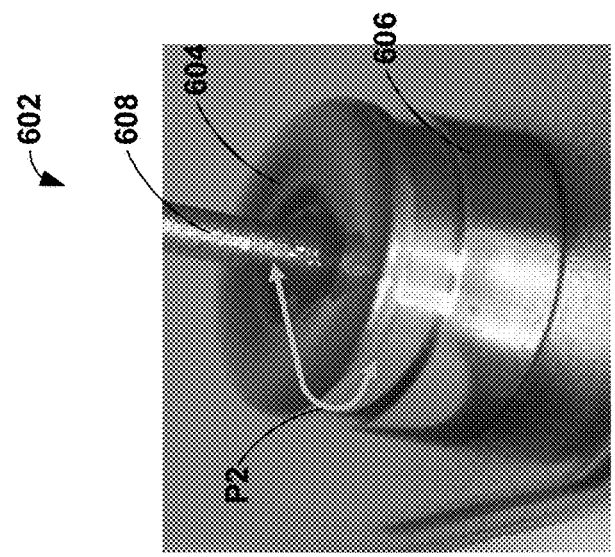
FIGS. 6A-6C are photographs illustrating an example feedthrough without a feedthrough insulator cap, after positioning a feedthrough insulator cap on a ferrule and a pin of an example battery, and after reflowing the feedthrough insulator cap onto the ferrule and the pin, respectively.
Figure 6B:
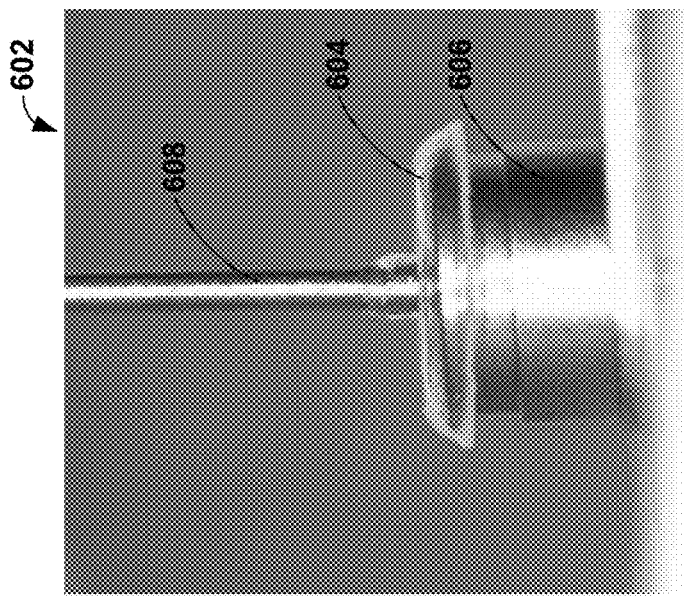
Figure 6A:
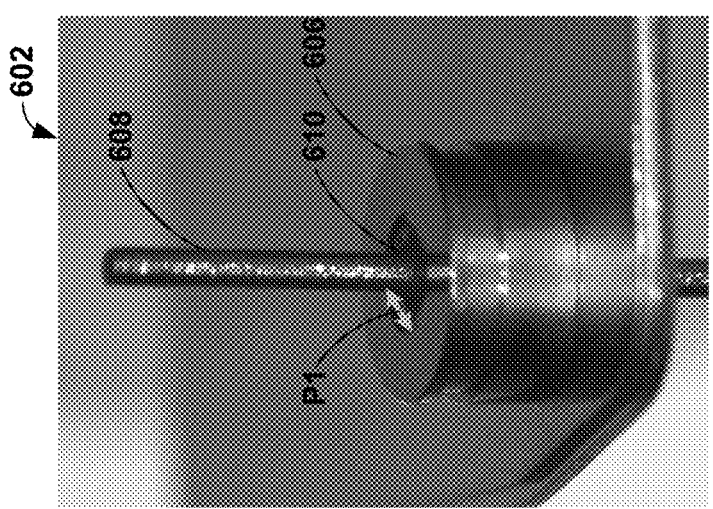

FIGS. 6A-6C are photographs illustrating an example feedthrough 602 without a feedthrough insulator cap, after positioning a feedthrough insulator cap 604 on a ferrule 606 and a pin 608 of an example battery, and after reflowing the feedthrough insulator cap 604 onto the ferrule 606 and the pin 608. As illustrated in FIG. 6A, exposed portions of ferrule 606 and pin 608 may define a path length P1. Path length P1 may traverse insulator 610. In some examples, path length P1 may be sufficiently short to enable electrical shorting via dendrite growth between ferrule 606 and pin 608 during operation of the battery. As illustrated in FIG. 6B, prior to reflow, feedthrough insulator cap 604 may be positioned over at least a portion of ferrule 606, at least a portion of insulator 610, and at least a portion of pin 608. As illustrated in FIG. 6C, after reflowing, feedthrough insulator cap 604 may lay flush against at least a portion of ferrule 606, at least a portion of insulator 610, and at least a portion of pin 608. After reflowing, exposed portions of ferrule 606 and pin 608 may define a path length P2. In some examples, path length P2 may be sufficiently long to reduce or prevent electrical shorting via dendrite growth between ferrule 606 and pin 608 during operation of the battery.

Figure 7:
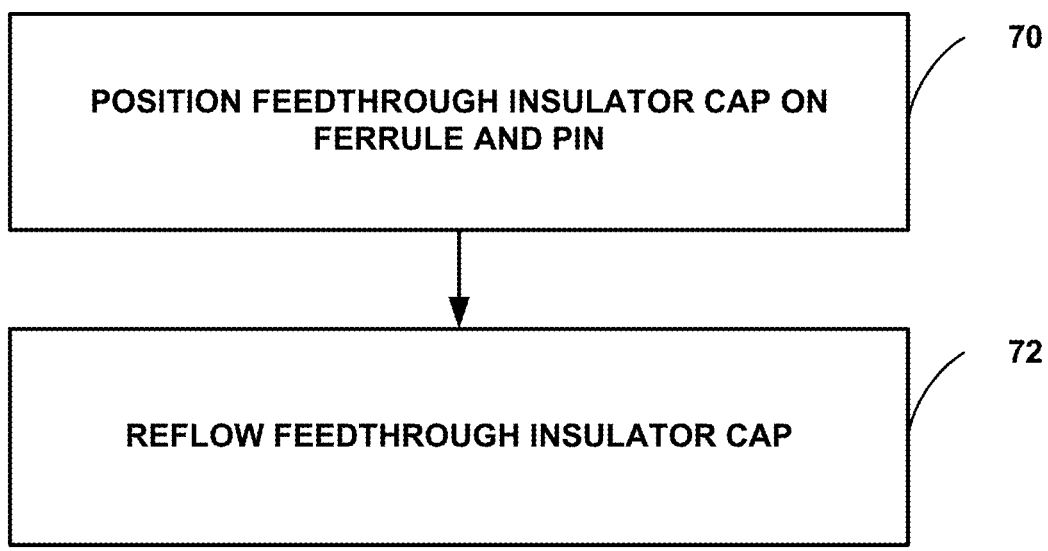
FIG. 7 is a flow diagram illustrating an example method for manufacturing an example battery.

The batteries described herein may be assembled using any suitable technique. FIG. 7 is a flow diagram illustrating an example method for manufacturing an example battery. The battery may be the same as or substantially similar to battery 26 discussed above with reference to FIGS. 1-5C. Although FIG. 7 is described with respect to battery 26, in other examples, the method of FIG. 7 may be used to assemble other batteries.

The technique may include forming a battery cell including anode stack 52, cathode stack 54, electrodes 56, and electrolyte 57 housed in enclosure 58. As discussed above, electrodes 56 may include one or more first electrodes (e.g., anodes) electrically coupled to anode stack 52 and one or more second electrodes (e.g., cathodes) electrically coupled to cathode stack 54, electrolyte 57 disposed between the first electrode(s) and the second electrode(s). Anode stack 52 may be electrically coupled to feedthrough pin 60, which extends from an interior segment of feedthrough pin 60, through a feedthrough member 64 extending through aperture 70 defined by enclosure 58, to an exterior portion of feedthrough pin 60.

The technique illustrated in FIG. 7 includes positioning feedthrough insulator cap 66 on feedthrough 64 of battery 26 (70). In some examples, the technique also may include forming feedthrough insulator cap 66. Forming feedthrough insulator cap 66 may include, for example, molding a polymeric material to define at least a portion of feedthrough insulator cap 66. In some examples, forming feedthrough insulator cap 66 may include cutting portions of the molded polymeric material, bonding (e.g., using an adhesive, sonic welding, or thermal welding) one or more molded components, or material addition to one or more molded components to define feedthrough insulator cap 66. In some examples, positioning feedthrough insulator cap 66 on feedthrough 64 of battery 26 may include injection molding feedthrough insulator cap 66 directly onto the feedthrough 64. Injection molding feedthrough insulator cap 66 directly onto feedthrough 64 may reduce manufacturing time and/or cost, reduce damage to preformed feedthrough insulator cap 66 when positioning on feedthrough 64, or both.

The technique illustrated in FIG. 7 includes heating feedthrough insulator cap 66 to reflow the material of feedthrough insulator cap 66 onto at least a portion of ferrule 72, at least a portion of insulator 74, and at least a portion of interior segment 86 of pin 60 configured to be disposed within an interior of a battery (72). In some examples, heating feedthrough insulator cap 66 may cause at least a portion of crown 92 to reflow in direction 102 by capillary action. In some examples, heating feedthrough insulator cap 66 may cause at least a portion of brim 90 (e.g., deflection 104) to reflow over an exterior lip 106 of ferrule 72.

Although not illustrated in FIG. 7, the technique may include electrically coupling anode stack 52 and cathode stack 54 to IMD 16. For example, anode stack 52 and cathode stack 54 may be electrically coupled to various circuitry within the housing of IMD 16. In examples in which IMD 16 includes a defibrillation device, anode stack 52 and cathode stack 54 may be coupled to charge storage circuitry of the defibration device used to store energy for delivery of a defibrillation shock via one or more leads coupled to IMD 16. In some examples, the technique may include implanting battery 26, and optionally IMD 16, in a body of patient 12.

Various examples of the disclosure have been described. Any combination of the described systems, operations, or functions is contemplated. These and other examples are within the scope of the following claims.

What is claimed is:

1. A method of assembling a battery comprising:
   positioning a feedthrough insulator cap on a feedthrough of the battery,
     wherein the feedthrough insulator cap comprises:
       a brim comprising an annular disk extending substantially within a plane, the brim having an interior edge and an exterior edge; and
       a crown integrally formed with the interior edge of the brim, wherein the crown extends above the plane of the brim in a first direction; and
     wherein the battery comprises:
       an enclosure defining the interior of the battery and a feedthrough aperture open to an exterior of the battery, the feedthrough comprising:
         a ferrule extending through the feedthrough aperture and coupled to the enclosure;
         an insulator extending through the ferrule to the exterior of the battery; and
         a pin extends through the insulator from the interior of the battery to the exterior of the battery, and wherein the insulator electrically insulates the pin from the ferrule;
       a first electrode disposed within the enclosure and electrically coupled to the pin;
       a second electrode disposed within the enclosure and separated a distance from the first electrode; and
       an electrolyte disposed between the first electrode and the second electrode; and
   heating the feedthrough insulator cap to reflow a material of the feedthrough insulator cap onto at least a portion of a ferrule, at least a portion of an insulator, and at least a portion of an interior segment of a pin.

2. The method of claim 1, wherein the ferrule comprises a cylindrical annulus having a radially exterior surface, a radially interior surface, and an interior annulus disposed within the enclosure, wherein the radially exterior surface is coupled to the feedthrough aperture, and wherein heating the feedthrough insulator cap causes the brim to extend over a lip of a radially exterior surface of the ferrule.

3. The method of claim 1, wherein the pin comprises an interior segment extending from the insulator to the first electrode, wherein heating the feedthrough insulator cap causes the crown to reflow on to at least a portion of the interior segment of the pin.

4. The method of claim 1, further comprising electrically coupling the first electrode and the second electrode to an implantable medical device.

5. The method of claim 1, further comprising implanting the high-rate primary battery in a body of a patient.

6. The method of claim 1, wherein positioning the feedthrough insulator cap on the feedthrough comprises injection molding the feedthrough insulator cap directly onto the feedthrough.

* * * * *